United States Patent [19]

Jacobs

[11] 4,393,884
[45] Jul. 19, 1983

[54] DEMAND INHALER FOR ORAL ADMINISTRATION OF TOBACCO, TOBACCO-LIKE, OR OTHER SUBSTANCES

[76] Inventor: Allen W. Jacobs, 12538 Oxnard St., #3, North Hollywood, Calif. 91606

[21] Appl. No.: 305,466

[22] Filed: Sep. 25, 1981

[51] Int. Cl.³ .................... A24D 1/00; A61M 15/00
[52] U.S. Cl. .......................... 131/273; 128/200.23; 128/202.21
[58] Field of Search .............. 128/200.23, 202.21; 131/273, 329, 330

[56] References Cited

U.S. PATENT DOCUMENTS

| | | | |
|---|---|---|---|
| 2,830,597 | 4/1958 | Kummli | 131/273 |
| 3,116,856 | 1/1964 | Prussin et al. | 128/200.23 |
| 3,631,856 | 1/1972 | Taylor | 131/273 |
| 3,721,240 | 3/1973 | Tamburri | 128/202.21 |
| 4,171,000 | 10/1979 | Uhle | 131/273 |

Primary Examiner—V. Millin
Attorney, Agent, or Firm—Keith D. Beecher

[57] ABSTRACT

An inhaler is provided for dispensing a pressurized substance, on demand, directly into the mouth of the user. The inhaler in one embodiment operates to dispense the substance when the user exerts a suction on one end thereof, and to terminate the dispensing process when the suction is removed. The inhaler may simulate a cigarette for the self-administration of tobacco or tobacco-like, or other substances, collectively to be referred to herein as nicotine. It is also contemplated that the inhaler may operate in response to other control effects exerted manually or by the mouth of the user, which control effects may be mechanically, thermally, chemically or electrically initiated.

Embodiments similar in appearance and utility to cigarettes, dispensing tobacco or tobacco-like products may be termed "nicarettes" denoting the generically new form of tobacco they represent. No limitation or definition of the scope or spirit of this invention is intended by the presentation of this herein coined word.

6 Claims, 6 Drawing Figures

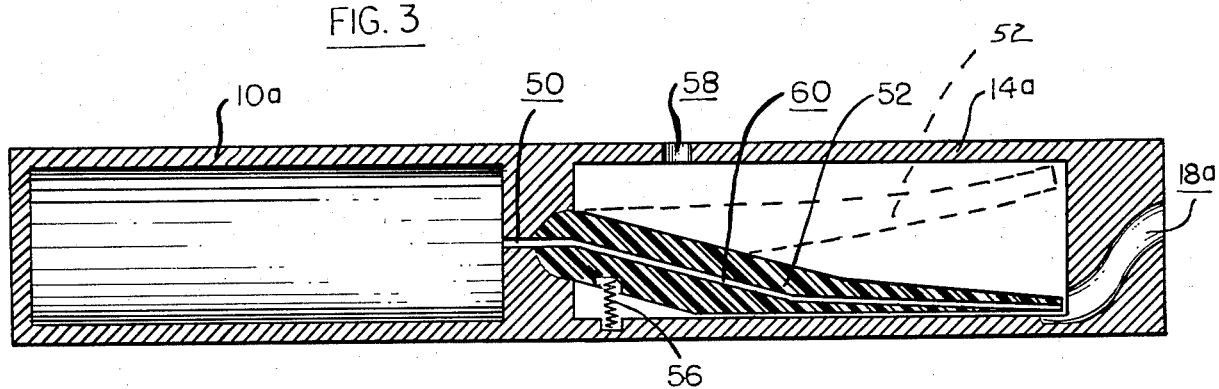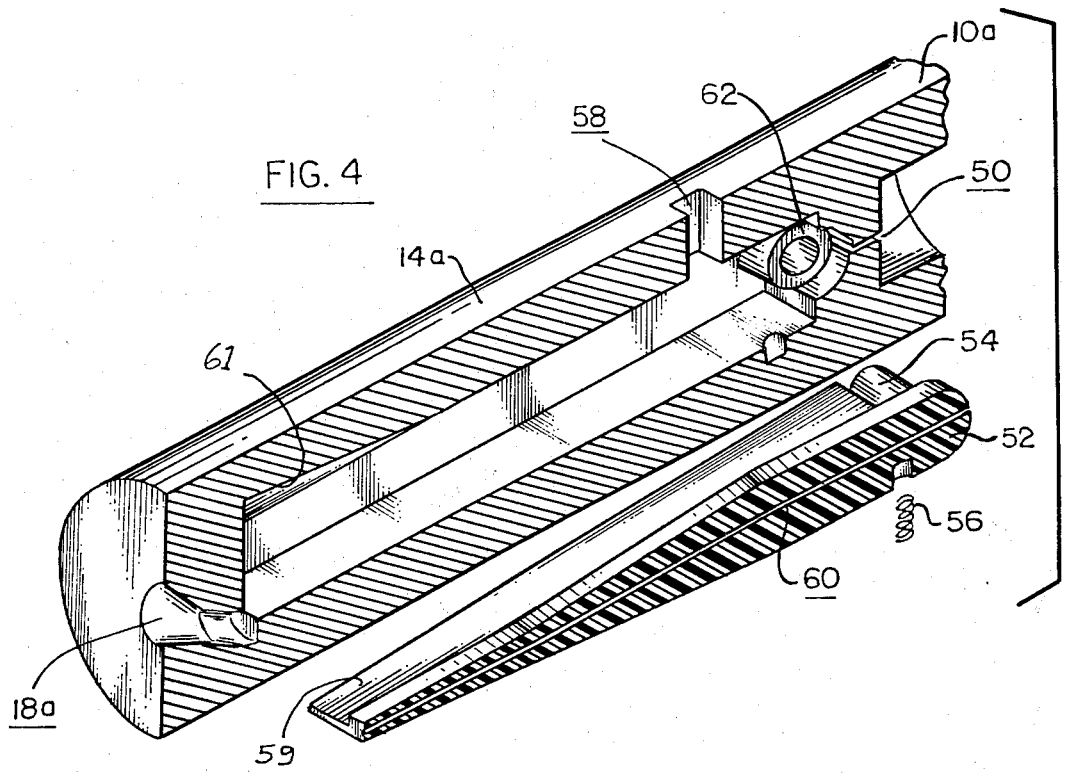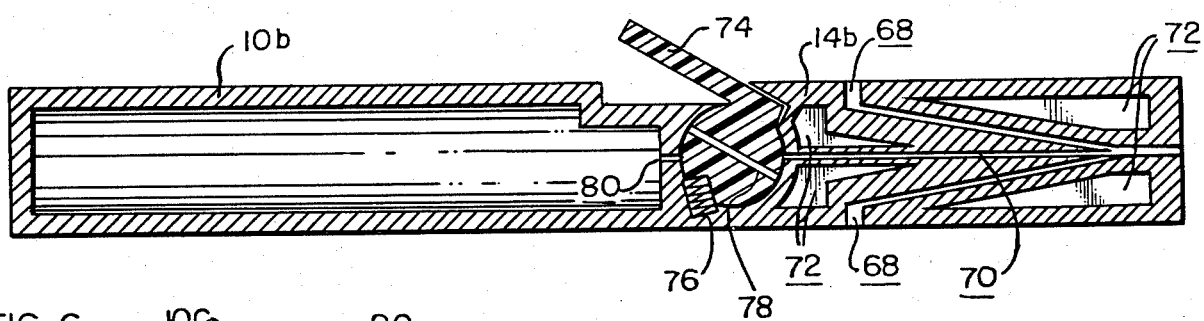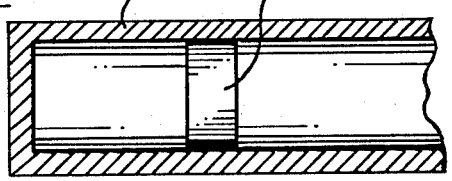

DEMAND INHALER FOR ORAL ADMINISTRATION OF TOBACCO, TOBACCO-LIKE, OR OTHER SUBSTANCES

RELATED PATENT APPLICATIONS

Application Ser. No. 29,749 filed Apr. 13, 1979 in the name of the present inventor, now abandoned.

BACKGROUND OF THE INVENTION

Copending Application Ser. No. 182,639 filed Aug. 29, 1980 in the name of the present inventor discloses a process for the administration of nicotine, or the like, to human beings, as a spray, vapor or related form, so as to serve as an alternative to smoking while still satisfying the user's addiction to nicotine, without many of the harmful by-products of actual smoking.

The instrument of the present invention, in one of its uses, may serve as a means for enabling a user to inhale nicotine formulations on demand, and in a manner which simulates the actual smoking of a cigarette. However, it will become evident as the description proceeds that the instrument of the invention has other uses. For example, the instrument may serve as a means for the ingestion of other substances, and provides a portable demand-type inhallation device which is capable of delivering such substances into the mouth of the user, either with or without the concomitant inhalation of a quantity of air mixed with the particular substance.

A feature of the instrument of the invention, in one of its embodiments, is the provision of a casing which includes a chamber in which the substance to be ingested is contained in a pressurized state, for example, by means of an aerosol propellant. When suction is applied to one end of the casing, the chamber is opened and the pressurized substance therein in dispensed into the mouth of the user either in a measured dose or as long as suction is applied. In this way, total control of the amount of the substance administered to the user is controlled by the user himself by the simple act of oral inhalation, and without the need for any other operation.

The instrument of the invention is not limited to the ingestion of "nicotine" since, as mentioned above, it may have other uses. For example, the instrument may be used as an effective means for administering both pharmacological and non-pharmacological agents and formulations which, in the practice of the art, are determined to be both useful and safe. The instrument may be used to dispense confections, breath fresheners, mouth washes, anesthetics, analgestics, antibiotics, antihistamines, tranquilizers, and the like.

BRIEF DESCRIPTION OF THE DRAWINGS

FIG. 3 is a sectional view of a second embodiment of the invention;

FIG. 4 is an enlarged sectional perspective view of the embodiment of FIG. 3;

FIG. 5 is a sectional view of yet another emodiment; and

FIG. 6 is a fragmentary section of a tubular housing in any of the foregoing embodiments and an internal piston to separate the propellant from the nicotine formulation itself.

DETAILED DESCRIPTION OF THE ILLUSTRATED EMBODIMENTS

Figure 1:
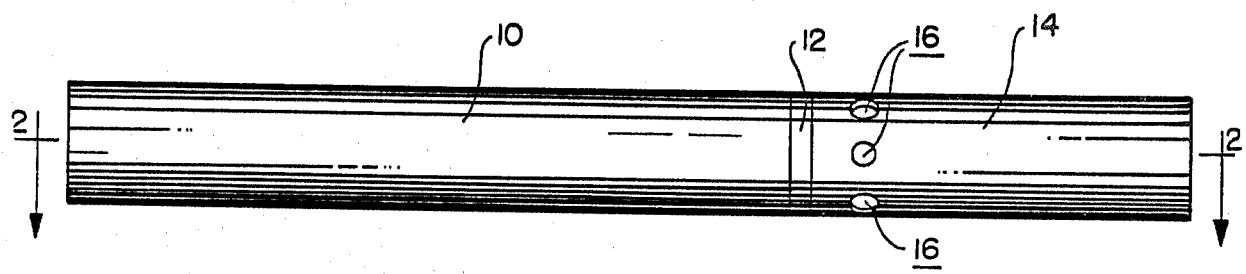
FIG. 1 is a side view of an inhaler constructed in accordance with one embodiment of the invention.
Figure 2:
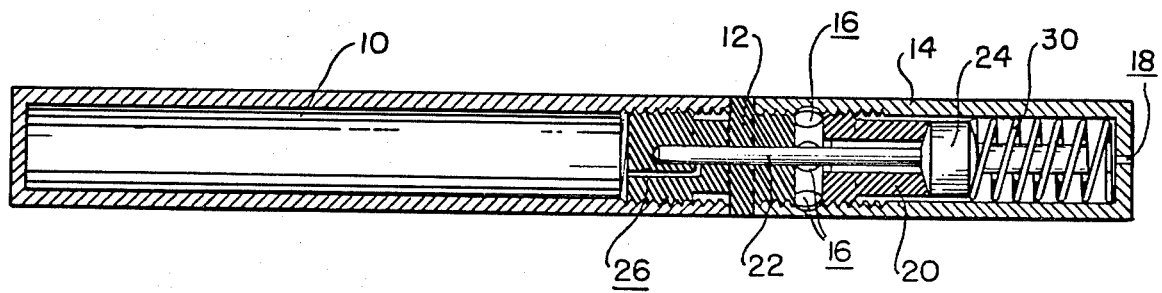
FIG. 2 is a section of the instrument of FIG. 1, taken along the line 2—2 of FIG. 1.

As shown in FIGS. 1 and 2, the instrument of the invention in the first embodiment includes a tubular housing 10 which is intended to contain a pressurized substance such as a nicotine formulation which, as mentioned above, may be mixed with a suitable aerosol propellant. A plug 12 is threaded into one end of the tubular housing 10, and a tubular mouthpiece 14 is threaded to the plug 12, so that the mouthpiece and tubular housing may be mounted in coaxial relationship with one another.

The tubular mouthpiece 14 may include a series of holes 16 which permit air to be drawn into the mouth of the user concomitantly with the pressurized substance in the chamber 10, whenever a suction is applied to the instrument.

As shown in FIG. 2, a hole 18 is provided in the distal end of the mouthpiece 14. A second plug 20 is threaded inside the mouthpiece 14, and the piston rod 22 of a piston 24 extends coaxially with the tubular housing 10 and tubular mouthpiece 14, through coaxial longitudinal passages in the plugs 12 and 20. A passage 26 extends from the interior of housing 10 through the plug 12, and the latter passage extends into the longitudinal passage in plug 12, as shown.

Figure 2A:
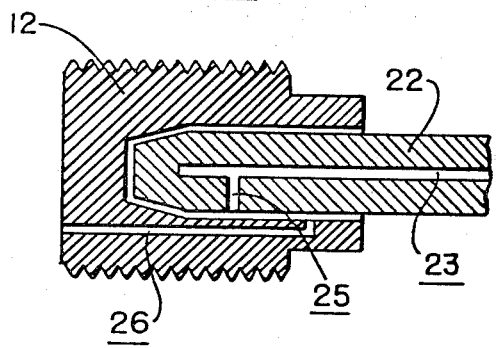
FIG. 2A is an enlarged view of a portion of the section of FIG. 2.

A spring 30 biases the piston 24 to the left in FIG. 1, so that the piston rod 22 normally closes the inner end of passage 26, as shown, for example, in FIG. 2A. The spring 30 is very weak, and has just sufficient force to hold the piston 24 in its closed position of FIGS. 2 and 2A. However, when the instrument is inserted into the mouth of the user, the user applies suction to the interior of the mouthpiece through the hole 18, the piston 24 is drawn to the right in FIGS. 2 and 2A. The piston rod 22 and piston 24 have a longitudinal passage 23 extending through it. Passage 23 communicates with a radial passage 25 in rod 22, so that when the piston 24 and rod 22 are drawn to the right in FIGS. 2 and 2A, the pressurized substance in the reservoir in tubular housing 10 can be drawn into the mouth of the user through the passages 26, 25, 23 and through hole 18.

At the same time, a quantity of air can also be drawn in through the holes 16 and through the hole 18 as a mixture with the pressurized substance.

When the suction is removed, the spring 30 again biases the piston 24 to the position shown in FIG. 2, in which piston rod 22 closes the end of passage 26, so that the release of the pressurized substance from the housing 10 is terminated.

It is to be understood that other mechanical assemblies may be used for causing the release of the pressurized substance in the housing 10 under the control of the mouth of the user. Also, this may be effectuated by chemical or electrical means, as well as thermal means, if so desired.

Figure 2B:
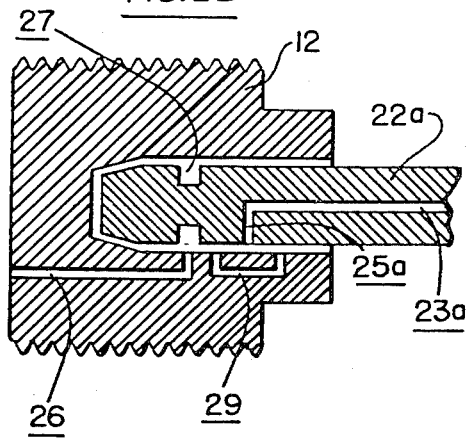
FIG. 2B is a modification of the view of FIG. 2A.

The rod 22 may be modified, as shown in FIG. 2B, so that a measured amount of the pressurized substance may be drawn into the mouth of the user when the piston is displaced to the right by the suction pressure exerted on it by the user through hole 18.

In the embodiment of FIG. 2B, the piston rod 22A is provided with a peripheral groove 27 which is aligned with the passage 26 when the piston is in its normal position to the left in FIGS. 2 and 2B. This peripheral groove is therefore filled with a predetermined quantity of the pressurized substance when the piston is in its normal position.

Then, when the piston is drawn to the right in FIGS. 2 and 2B by suction pressure exerted on it by the user, the peripheral groove 27 is lined up with one end of a passage 29 to be discharged through the longitudinal passage 23A into the mouth of the user since the radial passage 25A now becomes lined up with the other end of passage 29.

Then, when the suction pressure is removed, so that the piston is released, it returns to its position in FIG. 2B, and another measured quantity of the pressurized substance from the reservoir is fed into the peripheral groove 27, to be ingested the next time suction pressure is exerted on the piston.

It will be appreciated that in the embodiment of FIG. 2A, so long as suction pressure is exerted on the piston, a continuous stream of the pressurized fluid from the reservoir may be drawn into the mouth of the user. However, in the embodiment of FIG. 2B, when the piston 24 is drawn to the right by the suction pressure, only a measured quantity of the pressurized substance, that is, the quantity contained in the peripheral groove 27 may be drawn into the mouth of the user.

In some embodiments, the longitudinal passages 23 and 23a may be opened at both ends to prevent leakage pressure build-up between the piston rod 22 and 22a, and plug 12.

The embodiment of FIGS. 3 and 4 includes a tubular housing 10a which defines a reservoir for the nicotine, or other pressurized fluid, and the second embodiment also includes a mouthpiece 14a which is coaxial with the tubular housing 10a, and which may be integral with the tubular housing. An aperture 18a is provided at the end of mouthpiece 14a through which the user may draw the nicotine and/or other pressurized substances, when suction is applied.

A passageway 50 is provided in the partition between the reservoir within the tubular housing 10a and the chamber contained in the mouthpiece 14a. A member 52 is pivotally mounted within the mouthpiece 14a on a shaft 54 (FIG. 4) which is received, for example, in a bushing 62. The member 52 is normally spring-biased to an upper position in FIG. 3 by a spring 36, as indicated by the broken lines. The upper portion of the chamber within the mouthpiece 14a is exposed to the atmosphere through an air vent 58.

When suction is applied to the mouthpiece by the user through the aperture 18a, the resulting vacuum created within the lower portion of the chamber within the mouthpiece causes the member 52 to drop to the lower position in FIG. 3 against the force of spring 56, as indicated by the solid lines. When the member 52 is in the lower position in FIG. 3, an internal longitudinal passage 60 is aligned with passage 50 so that the pressurized nicotine, and/or other substances within the reservoir may be drawn into the mouth of the user through aperture 18a.

The member 52 may be shaped, so that a portion of the air contained in the upper part of the chamber within the mouthpiece 14a is also drawn into the aperture 18a over a fin 59 of the member 52 when suction is applied to the aperture, to be mixed with the pressurized substance. The thin edge of the fin 59 most distal to the pivotal shaft 54 and the recess 61 in the tubular housing 10a allow maximal pivotal movement of the member 52, combined with maximal mechanical advantage in aligning passage 60 with passage 50.

Therefore, in the embodiment of FIG. 3, whenever the user sucks on the right-hand end of the instrument, and resulting suction pressure applied to the interior of the mouthpiece 14a through the opening 18a causes the member 52 to drop to its lower position in FIG. 3, in which its internal passage 60 is aligned with passage 50, so that the pressurized substance in the reservoir within tubular housing 10a may be drawn into the mouth of the user. Whenever the suction is removed, however, spring 56 promptly returns the member 52 to its upper position in FIG. 3, during which the passage 60 is no longer aligned with passage 50 and the contents of the reservoir are sealed. The spring 56 may be shaped as deemed necessary and may be an integral part of either the member 52 or housing 10a. It may also be made of the same material as either.

In the embodiment of FIG. 5, a tubular housing 10b defines an integral reservoir, and a tubular mouthpiece 14b is formed integrally with the tubular housing in coaxial relationship. The mouthpiece 14b has a longitudinal passage extending through it, which is designated 70. To lighten the structure, dead spaces 72 may be included into the mouthpiece 14b. One or more air intakes 68 may coterminate with or terminate near the longitudinal passage 70 for air mixture as deemed desirable. In the absence of these intakes 68, the dead spaces 72 separated in FIG. 5 by the air intakes 68 may each be enlarged and joined longitudinally.

To operate the dispenser, the mouthpiece 14b is inserted into the mouth of the user and, to discharge the contents of the reservoir within tubular housing 10b into the mouth of the user, a spring-loaded rotary valve 74 is depressed against the tension of a spring 76 so as to line up a passage 78 with a passage 80 at the end of the tubular housing and passage 70 extending through the mouthpiece.

It is within the scope of the invention to provide some embodiments with a non-rotary valve wherein passage 78 is at all times parallel to passages 70 and 80 but is misaligned laterally with them in the closed position. The passage 78 is brought into coaxial alignment when a button with perpendicular travel, replacing the lever of rotary valve 74 is depressed.

It is to be understood that in both the embodiments of FIGS. 3 and 5, an arrangement similar in function to that shown in FIG. 2B may be utilized so that in each instance, a measured amount only of the contents of the reservoir may be discharged into the mouth of the user. In FIG. 5, this arrangement may be accomplished simply by misaligning passage 80 slightly in the direction of the lever on rotary valve 74 such that passages 78 and 80 pass into alignment filling passage 78 as the lever 74 is first depressed. On continued movement of the lever 74, passage 78 passes beyond alignment with passage 80 and into alignment with passage 70, discharging its contents into passage 70. In like manner, non-rotary valve embodiments may utilize this measured dispensation arrangement.

In the fragmentary sectional view of FIG. 6, a tubular housing 10C is illustrated which defines an internal reservoir for the pressurized substance, such as a nicotine formulation. However, in the latter embodiment a piston 90 is provided which is slidable in the reservoir, and which separates the propellant from the substance to be discharged. The propellant is placed to the left of the piston, and serves to force the piston against the substance in the reservoir to the right of the piston, so as to create a pressurized condition.

This is often desirable in various embodiments to permit discharge of the contents of the dispenser from any position it is in, independent of gravity. It also provides for mechanical assistance in pressurizing the substances to be dispensed, such as through use of a spring against the piston, in the propellant compartment formed by the piston itself. In translucent or clear walled reservoirs, a marked or unmarked piston provides a visual measure of the remaining contents, additionally, propellants with which it is undesirable to mix the dispensed contents may be separated from them by means of a piston. Multiple propellant systems, thus, become feasible wherein some propellants may be included in the dispensed contents while others are separated.

By illustrative example only, a gas (such as $CO_2$) may be added to the dispensed contents while other propellants (such as $N_2$), isobutane, Freon ®, or propane) may be separated by means of a piston. As necessary, even multiple piston systems are within the scope of the invention.

Separation in any of the above circumstances may be accomplished by means of one or more open ended or fully closed flexible bags containing either propellant, contents to be dispensed, or both.

It is within the spirit of the invention to extend the mouthpiece portion of some embodiments to provide for a bit, shaped similarly to those on many pipes and cigars. It may be added to the end, if desired, or an integral part of the dispenser as determined desirable in the practice of the art.

It will be appreciated that while particular embodiments of the invention have been shown and described, modifications may be made. It is intended in the claims to cover the spirit and scope of the invention.

What is claimed is:

1. A dispenser for introducing a substance into the mouth of a user comprising: means defining a reservoir for containing the substance in a pressurized state and also defining an inner chamber in axial alignment with the reservoir and having an apertured end portion at the end thereof opposite to said reservoir; a partition interposed between said reservoir and said inner chamber and having an aperture therein; an elongated member mounted for reciprocal pivotal movement in said inner chamber and having a first angular position in said inner chamber in which the aperture in the partition is closed, and said elongated member having a second angular position within said inner chamber in which the aperture is open for releasing the substance from the reservoir to the apertured end portion of said inner chamber; and in which the user selectively introduces suction to the inner chamber through the apertured end portion thereof to move the elongated member from its first angular position to its second angular position so as to cause the aperture in said partition to open to enable the substance in the reservoir to be introduced into the mouth of the user through said apertured end portion under the control of the user.

2. The dispenser defined in claim 1, in which said means defining said reservoir comprises a tubular housing, and in which said means defining said inner chamber comprises a tubular housing coaxial with said first-named tubular housing.

3. The dispenser defined in claim 1, in which said means defining said inner chamber has at least one opening therein to permit air to be introduced into the mouth of the user concomitantly with the pressurized substance.

4. The dispenser defined in claim 1, and which includes spring means engaging said elongated member to bias the elongated member to its first angular position.

5. The dispenser defined in claim 1, and which includes means positioned in the reservoir serving to separate the pressurized substance from a propellant.

6. The dispenser defined in claim 1, and which includes a passage extending through the elongated member from one end thereof to the other, and through which the substance from the reservoir is drawn by the suction of the user when the elongated member is moved to its second angular position.

* * * * *